US010307430B2

(12) United States Patent
Polak et al.

(10) Patent No.: US 10,307,430 B2
(45) Date of Patent: Jun. 4, 2019

(54) KATP ANTAGONISTS (GLIBENGLAMID) FOR USE FOR PROMOTING GROWTH AND/OR TREATING HYPERGLYCAEMIA OF A PREMATURE INFANT

(75) Inventors: Michel Polak, Paris (FR); Marianne Berdugo Polak, Paris (FR)

(73) Assignee: ASSISTANCE PUBLIQUE—HOPITAUX DE PARIS, Paris (FR)

( * ) Notice: Subject to any disclaimer, the term of this patent is extended or adjusted under 35 U.S.C. 154(b) by 0 days.

(21) Appl. No.: 14/115,103

(22) PCT Filed: May 2, 2012

(86) PCT No.: PCT/EP2012/057995
§ 371 (c)(1),
(2), (4) Date: Nov. 1, 2013

(87) PCT Pub. No.: WO2012/150245
PCT Pub. Date: Nov. 8, 2012

(65) Prior Publication Data
US 2014/0051761 A1 Feb. 20, 2014

(30) Foreign Application Priority Data
May 3, 2011 (EP) ..................... 11305520

(51) Int. Cl.
*A61K 31/64* (2006.01)
*A61K 31/451* (2006.01)
*A61K 9/00* (2006.01)

(52) U.S. Cl.
CPC ............ *A61K 31/64* (2013.01); *A61K 9/0053* (2013.01); *A61K 31/451* (2013.01)

(58) Field of Classification Search
CPC ................................ A61K 31/46; A61K 31/64
See application file for complete search history.

(56) References Cited

U.S. PATENT DOCUMENTS 5,258,185 A * 11/1993 Bauer et al. .................. 424/484
6,989,367 B2 * 1/2006 Fruebis et al. ................ 514/4.8

FOREIGN PATENT DOCUMENTS

EP          1884 244        * 2/2008
WO     WO2009/097443       * 8/2009

OTHER PUBLICATIONS

Olsen, I.E. et al, Pediatrics, vol. 125, No. 2, Feb. 2010, p. e214-e224.*
Heinze, E. et al., Exp. Clin. Endocrinol. 103:260-265.*
Galal, S. et al.,Formulation of fast release glibenclamide liquid and semi-solid matrix filled capsules, Acta Pharm Mar. 2003: 53(1): 57-64.*

Aguilar-Bryan, et al., Endocrine Reviews, May 2008, 29(3): 265-291.*
Hays, et al., Pediatrics, vol. 118, No. 5, Nov. 2006, p. 1811-1818.*
Heinze, E. et al. "Insulin Secretion in Growth Hormone-Deficient Children and the Effect of the Sulfonylurea Drug Glibenclamide on Linear Growth" *European Journal of Pediatrics*, 1978, pp. 41-48, vol. 128.
Mohnike, K. et al. "Glibenclamidtherapie zur Waehstumsbeeinflussung beim HGH-Mangel" *Experimental and Clinincal Endrinology*, Jan. 1, 1982, pp. 73-74, vol. 80, No. 1.
Amendt, P. et al. "Der Effekt von Sulfonylharnstoffen auf Insulinsekretion und Wachstumsraten bei Kindern mit hypothalamisch-hypophysarem Minderwuchs" *Kinderaerztliche Praxis*, Sep. 1, 1981, pp. 473-479, vol. 49, No. 9.
Heinze, E. et al. "Glibenclamide stimulates growth of human chondrocytes by IGF I dependent mechanisms" *Experimental and Clinical Endocrinology & Diabetes*, 1995, pp. 260-265, vol. 103, No. 4.
Nitowsky, H. et al. "Studies on oxidative drug metabolism in the full-term newborn infant" *The Journal of Pediatrics*, Dec. 1966, pp. 1139-1149, vol. 69, No. 6.
Wendelin, G. et al. "Neonatal Diabetes Mellitus: Treatment with Sulfonylurea in a Preterm Born Infant" *Klinische Padiatrie*, Mar. 2009, p. 1, vol. 221, No. 2.
Written Opinion in International Application No. PCT/EP2012/057995, dated Aug. 14, 2012, pp. 1-10.
Polak, M. et al. "Neonatal diabetes mellitus: a disease linked to multiple mechanisms" *Orphanet Journal of Rare Diseases*, 2007, pp. 1-11, vol. 2, No. 12.
Mitanchez-Mokhtari, D. et al. "Both Relative Insulin Resistance and Defective Islet β-Cell Processing of Proinsulin Are Responsible for Transient Hyperglycemia in Extremely Preterm Infants" *Pediatrics*, Mar. 2004, pp. 537-541, vol. 113, No. 3.
Busiah, K. et al. "Differentiating Transient Idiopathic Hyperglycaemia and Neonatal Diabetes Mellitus in Preterm Infants" *Hormone Research in Paediatrics*, 2015, pp. 68-72, vol. 84.
Hawdon, J.M. et al. "The role of pancreatic insulin secretion in neonatal glucoregulation, II. Infants with disordered blood glucose homoeostasis" *Archives of Disease in Childhood*, 1993, pp. 280-285, vol. 68.
Babenko, A.P. et al. "Activating Mutations in the ABCC8 Gene in Neonatal Diabetes Mellitus" *The New England Journal of Medicine*, Aug. 3, 2006, pp. 456-466, vol. 355, No. 5.
Beardsall, K. et al. "Early Insulin Therapy in Very-Low-Birth-Weight Infants" *The New England Journal of Medicine*, Oct. 30, 2008, pp. 1873-1884, vol. 359, No. 18.
Beardsall, K. et al. "Prevalence and Determinants of Hyperglycemia in Very Low Birth Weight Infants: Cohort Analyses of the NIRTURE Study" *The Journal of Pediatrics*, 2010, pp. 715-719 and 713.e1-713.e3, vol. 157, No. 5.
Røder M. E. et al., "Intact Proinsulin and β-Cell Function in Lean and Obese Subjects With and Without Type 2 Diabetes" *Diabetes Care*, Apr. 1999, pp. 609-614, vol. 22, No. 4.

(Continued)

*Primary Examiner* — San Ming R Hui
(74) *Attorney, Agent, or Firm* — Saliwanchik, Lloyd & Eisenschenk

(57) ABSTRACT

The present invention relates to pharmaceutical compositions comprising an ATP-sensitive potassium (K ATP) channel antagonist (e.g., sulfonylureas, meglitinides) and methods for treating hyperglycaemia and/or promoting growth of a premature and/or small for gestational age infant.

15 Claims, No Drawings

(56) References Cited

OTHER PUBLICATIONS

Retnakaran, R. et al. "The Impact of Insulin Resistance on Proinsulin Secretion in Pregnancy" *Diabetes Care*, Nov. 2005, pp. 2710-2715, vol. 28, No. 11.
Lewis, G.F. et at. "Hepatic Glucose Production Is Regulated Both by Direct Hepatic and Extrahepatic Effects of Insulin in Humans" *Diabetes*, Apr. 1996, pp. 454-462, vol. 45.
Rachman, J. et al. "Relative Hyperproinsulinemia of NIDDM Persists Despite the Reduction of Hyperglycemia With Insulin or Sulfonylurea Therapy" *Diabetes*, Oct. 1997, pp. 1557-1562, vol. 46.
Vauhkonen, I.K.J. et al. "Hyperproinsulinemia is not a characteristic feature in the offspring of patients with different phenotypes of type II diabetes" *European Journal of Endocrinology*, 2000, pp. 251-260, vol. 143.
Cowett, R.M. et al. "Persistent Glucose Production during Glucose Infusion in the Neonate" *Journal of Clinical Investigation*, Mar. 1983, pp. 467-475, vol. 71.
Mitanchez, D. et al. "Glucose Regulation in Preterm Newborn Infants", *Hormone Research*, Jun. 20, 2007, pp. 265-271, vol. 68.

* cited by examiner

KATP ANTAGONISTS (GLIBENGLAMID) FOR USE FOR PROMOTING GROWTH AND/OR TREATING HYPERGLYCAEMIA OF A PREMATURE INFANT

CROSS-REFERENCE TO RELATED APPLICATION

This application is the U.S. national stage application of International Patent Application No. PCT/EP2012/057995, filed May 2, 2012.

FIELD OF THE INVENTION

The present invention relates to the field of medicine, in particular of pediatrics.

The present invention relates to compositions and methods for treating hyperglycaemia and/or promoting catch-up growth of a premature and/or small for gestational age infant.

BACKGROUND OF THE INVENTION

In Europe and many developed countries, the preterm birth rate is generally 5-6%, and in the USA it has even risen to 12-13% in the last decades. By gestational age, 5% of preterm births occur at less than 28 weeks (extreme prematurity), 15% at 28-31 weeks (severe prematurity), 20% at 32-33 weeks (moderate prematurity), and 60-70% at 34-36 weeks (late preterm). Preterm birth may follow preterm labor or premature rupture of membranes. They also may be induced for obstetrical reasons such as infection, intrauterine growth retardation or preeclampsia. However, in many situations, the cause for preterm birth remains elusive and unknown.

Premature infants are at greater risk for short and long term complications. In particular, during the first week of life, many preterm infants, particularly infants born at less than 32 gestational weeks and very low birth weight infants (birth weight of less than 1,500 g), develop hyperglycaemia. The hyperglycaemia is particularly common on day 2 and 3 after birth and is associated with both mortality and morbidity. The pathogenesis of this hyperglycaemia is complex and not clear. However, it seems to be related to defective islet beta-cell processing of proinsulin and to early and persistent reduction in insulin sensitivity of preterm infants (Mitanchez, 2008). Intracellular glucose deprivation, a consequence of low postnatal insulin levels, may also initiate counterregulatory responses and catabolism, leading to hyperglycaemia.

In addition to hyperglycaemia, a large proportion of preterm infants show evidence of postnatal growth impairment irrespective of whether birth weight was appropriate (AGA) or small for gestational age (SGA). The timing and magnitude of catch-up growth is very variable and long term studies suggest that final height may be significantly affected (Finken et al., 2006). For full-term SGA infants, the majority achieved catch-up growth during the first 2 years of life, and most of the increase in height occurred by several months of age, mostly by six months. However, SGA children who remained short at 2 years of age (about 10%) had a higher risk of short stature later in life (Albertsson-Wikland et al., 1998).

Previous studies on circulating growth factors related to in-utero or ex-utero growth restraints showed that IGF-I and IGF-2 mediates the majority of the growth-promoting effects of growth hormone (GH) before birth in humans, whereas IGF-I and growth hormone are the major post-natal factors. Indeed, deletions in the IGF-1 gene result in severe pre- and post-natal growth and developmental defects and in mental retardation (Woods et al., 1996). Furthermore, it was also demonstrated that, at birth, when analyzed according to gestational age, serum insulin-like growth factor-I (IGF-I) level was decreased in intrauterine growth-retarded children as compared with normal neonates. During the first 3 months of life, a positive correlation was also found between IGF-I increment and weight gain (Leger et al., 1996).

IGF-1 is a trophic factor that circulates at high levels in the blood stream. The majority of circulating IGF-1 is produced in the liver. However, many other tissues including bone, adipose tissue, kidney, and muscle also produce IGF-1 and are sensitive to its action, especially during postnatal development. The regulation of IGF-1 production in hepatic tissue is mainly mediated by growth hormones and insulin. In turn, IGF-1 feeds back to suppress growth hormones and insulin release (Pavelic et al., 2007).

A pilot study showed that intravenous administration of insulin throughout the first week of life in very low birth weight infants improves blood glucose control and increases IGF-I levels (Beardsall et al., 2007). This study led to the Neonatal Insulin Therapy in Europe (NIRTURE) Trial involving 194 very-low-birth-weight infants and aiming to determine whether early insulin replacement reduced hyperglycaemia and affected outcomes in such neonates. Results of this trial confirmed that early insulin replacement by intravenous administration improved glucose control and reduced weight loss in the first week of life but also increased risk of hypoglycaemia (Beardsall et al., 2008). This trial was finally stopped because of concerns that the primary outcome of mortality at the expected date of delivery was ineffective and because of concerns of potential harm. Administration of insulin therapy in preterm and/or low birth weight infants thus remains controversial.

Accordingly, there is a strong need for an alternative safe method for treating hyperglycaemia in preterm or low birth weight infants and promoting their catch-up growth.

SUMMARY OF THE INVENTION

The inventors have herein demonstrated that, in preterm and/or small-for-gestational-age infants, insulin infusion can be replaced by enteral administration of an antagonist of the ATP-sensitive potassium ($K_{ATP}$) channel for treating hyperglycaemia and promoting catch-up growth.

Accordingly, in a first aspect, the present invention concerns a pharmaceutical composition suitable for enteral administration of a $K_{ATP}$ channel antagonist for use for treating hyperglycaemia and/or promoting growth of a premature and/or small-for-gestational-age infant.

Preferably, the infant weights less than 2,500 g at birth, more preferably less than 1,500 g at birth. Preferably, the premature infant is born at less than 32 weeks gestation, more preferably at less than 28 weeks gestation.

The $K_{ATP}$ channel antagonist may be selected from the group consisting of sulfonylureas and meglitinides, and any combination thereof. In particular, the $K_{ATP}$ channel antagonist may be selected from the group consisting of glibenclamide, acetohexamide, carbutamide, glibornuride, chlorpropamide, tolbutamide, tolazamide, glipizide, gliclazide, gliquidone, glycopyramide, glisoxepide, glimepiride repaglinide, nateglinide and mitiglinide. Preferably, the $K_{ATP}$ channel antagonist is glibenclamide.

The pharmaceutical composition may be in any form suitable for enteral administration. Preferably, the pharmaceutical composition is in a liquid form. More preferably, the pharmaceutical composition is a suspension of micronized particles of the $K_{ATP}$ channel antagonist, preferably of glibenclamide.

In another aspect, the present invention concerns the use of a $K_{ATP}$ channel antagonist for the preparation of a medicament suitable for enteral administration for treating hyperglycaemia and/or promoting growth in preterm and/or SGA infants.

In a further aspect, the present invention also concerns a method for treating hyperglycaemia and/or promoting growth in preterm and/or SGA infants, wherein the method comprises enterally administering a therapeutically effective amount of a $K_{ATP}$ channel antagonist to infants in need thereof.

DETAILED DESCRIPTION OF THE INVENTION

Several previous studies suggested that insulin therapy, when used with caution, is efficient to reduce endogenous glucose production in preterm newborn infants (Mitanchez, 2007; Beardsall and Dunger, 2008). However, the results of the large European NIRTURE trial, as described above, seem to indicate that in fact no clinical benefit could be obtained with early insulin therapy in infants with very low birth weight (Beardsall et al., 2008).

The inventors are convinced that negative results obtained in this trial are essentially due to the intravenous administration of insulin. Indeed, the normal physiological delivery of insulin into the portal circulation ensures that the liver is exposed to higher insulin concentrations than the peripheral circulation. Injections of insulin into the peripheral circulation do not replicate this normal delivery and result in peripheral hyperinsulinemia which is known to be associated with hypoglycemia and other adverse metabolic effects. Consequently, intravenous administration of insulin in preterm infants is very difficult and needs extreme caution.

Many attempts to produce an oral insulin formulation have been reported over the last three decades. However, none has provided both an adequate shield against proteolytic digestion and an effective aid to absorption to give reasonable bioavailability.

In order to obtain beneficial effects of insulin therapy in preterm infants without adverse effects of insulin infusions, the inventors have found that a $K_{ATP}$ channel antagonist can be enterally administered to these infants.

It is well established that insulin secretion from fetal human pancreatic β cells is poorly responsive to glucose, compared to adult cells. However, previous studies demonstrated that human fetal β cells obtained from 14 to 20 week gestational fetus are able to secrete insulin in response to KCl, glipizide, BAY K8644 and cAMP (Weinhaus et al., 2003). These results suggest that pancreatic β cells of preterm infants are sensitive to insulin secretagogue and can efficiently secrete endogenous insulin when stimulated.

Accordingly, in a first aspect, the present invention concerns a pharmaceutical composition suitable for enteral administration and comprising a $K_{ATP}$ channel antagonist for use for treating hyperglycaemia and/or promoting growth of a premature and/or small-for-gestational-age (SGA) infant.

The infant may be a premature or preterm infant. The terms "premature infant" and "preterm infant" are herein used interchangeably. A premature infant is an infant who is born at less than 37 weeks gestational age. Preferably, the premature infant is born at less than 32 weeks gestational age. More preferably, the premature infant is born at less than 28 weeks gestational age. In a particular embodiment, the premature infant is born between 32 and 24 weeks gestational age. In another particular embodiment, the premature infant is born between 28 and 24 weeks of gestational age.

The infant may be a small-for-gestational-age (SGA) infant. The term "small-for-gestational-age infant" or "SGA infant" is herein used to refer to an infant whose birth weight, length, or head circumference lies below the 10th percentile for that gestational age. The SGA infant may be born full-term or preterm. A baby born within the normal range of mass for that gestational age is known as appropriate for gestational age (AGA) infant.

Preferably, the preterm or SGA infant is a low birth weight infant, i.e. an infant who weighs less than 2,500 g at birth. More preferably, the preterm or SGA infant is a very low birth weight infant, i.e. an infant who weighs less than 1,500 g at birth.

In an embodiment, the infant is a premature infant with hyperglycaemia. In this embodiment, the infant may be an AGA or SGA infant. In a particular embodiment, the infant is a SGA premature infant with hyperglycaemia.

In another embodiment, the infant is an AGA premature infant with preterm growth restraint. The term "AGA premature infant with preterm growth restraint" refers to a premature infant born with appropriate size for gestational age but who grows poorly in the first postnatal weeks or months (i.e. preterm growth restraint).

In a further embodiment, the infant is a SGA full-term infant with or without hyperglycaemia, preferably with hyperglycaemia.

In a particular embodiment, the infant is younger than 6 months, 3 months, 2 months or one month. In a preferred embodiment, the infant is younger than 3 weeks, preferably 2 weeks, more preferably one week.

In a particular embodiment, the infant has not yet reached the expected date of delivery.

As used herein, the term "hyperglycaemia" refers to a condition in which an excessive amount of glucose circulates in the blood plasma. For newborn infants, and in particular preterm and SGA infants, this term is statistically defined as blood glucose concentration greater than 7 mmol/L or plasma glucose concentration greater than 8.25 mmol/L. Preferably, this term refers to a blood glucose concentration greater than 10 mmol/L, more preferably greater than 12 mmol/L.

As used herein, the term "$K_{ATP}$ channel antagonist" refers to a compound that stimulates endogenous insulin secretion by binding and closing ATP-sensitive potassium ($K_{ATP}$) channel (SUR1/Kir6.2). This $K_{ATP}$ channel antagonist may be selected from the group consisting of sulfonylureas and meglitinides, and any combination thereof. In particular, the $K_{ATP}$ channel antagonist may be selected from the group consisting glibenclamide (glyburide), acetohexamide, carbutamide, glibornuride, chlorpropamide, tolbutamide, tolazamide, glipizide, gliclazide, gliquidone, glyclopyramide, glisoxepide, glimepiride, repaglinide, nateglinide and mitiglinide, and any combination thereof. In a preferred embodiment, the $K_{ATP}$ channel antagonist is selected from the group consisting of sulfonylureas, in particular glibenclamide, acetohexamide, carbutamide, glibornuride, chlorpropamide, tolbutamide, tolazamide, glipizide, gliclazide, gliquidone, glyclopyramide, glisoxepide and glimepiride, and any combination thereof. In a more preferred embodiment, the $K_{ATP}$ channel antagonist is glibenclamide. The pharmaceutical composition may comprise one or several $K_{ATP}$ channel antagonists.

The pharmaceutical composition may also comprise one or several additional active substances. These additional active substances may be used to improve blood glucose control and/or to further promote growth. An additional active substance that improves blood glucose control may be, for example, selected from the group consisting of glucose, glucagon, insulin and leptin. An additional active substance that promotes growth of the infant may be, for example, selected from the group consisting of IGF-I, Mecasermin (recombinant human IGF-I) and growth hormone.

As used herein, the term "enteral administration" refers to administration through the gastrointestinal tract. In particular, enteral administration comprises administration by mouth (orally) and administration by nasogastric feeding tube or gastric feeding tube.

$K_{ATP}$ channel antagonists, in particular sulfonylureas, are typically poorly water soluble, and are commonly given as pills or in other solid form. However, these forms cannot be used for preterm or SGA infants. In order to be suitable for enteral administration in these infants, the pharmaceutical composition can be formulated into dosage oral forms such as powders and liquid preparations. Liquid preparations may be suspensions, syrups or concentrated drops.

Preferably, the pharmaceutical composition is a suspension of micronized particles of the $K_{ATP}$ channel antagonist. More preferably, the pharmaceutical composition is a suspension of micronized particles of glibenclamide.

Suitable liquid formulations of sulfonylurea or meglitinide drugs, and in particular of glibenclamide, are described for example in the international patent applications WO 01/51463 and WO 2009/097443.

The pharmaceutical composition may comprise water soluble excipient(s). Suitable water soluble excipients include, but are not limited to, mannitol, sorbitol, xylitol lactose, sucrose, maltose, glucose, maltodextrins, polyethylene glycol (PEG 300 or PEG 400), propylene glycol, glycerine, N-methyl-2-pyrrolidone, dimethylacetamide, dimethylsulfoxide, polyalkylene glycols, cyclodextrins, chitosan, or N-methyl-2-pyrrolidone. The pharmaceutical composition may also comprise surfactant(s) such as Tween 80, Polysorbate 80 or ethoxylated castor oils.

In a preferred embodiment, the pharmaceutical composition of the invention is administered directly into the stomach of the infant, preferably using minimal enteral feeding gastric tube. The minimal enteral feeding is a practice wherein minute volumes of feeds are given to the baby in order to stimulate the development of the immature gastrointestinal tract of the preterm infant. Recommended volume is 10-15 ml/kg/day, divided into equal aliquots and administered by gavage feeding. The gavage feeding of a newborn is a procedure in which a tube passed through the nose or mouth into the stomach is used to feed a newborn.

The $K_{ATP}$ channel antagonist may be administered as a single dose or in multiple doses. Each unit dosage may contain, for example, from 0.005 mg to 2 mg, preferably from 0.01 mg to 1 mg, of a $K_{ATP}$ channel antagonist. In a preferred embodiment, the $K_{ATP}$ channel antagonist is glibenclamide and each unit dosage contains from 0.01 mg to 1 mg. Unit dosage may be, for example, a vial, an ampoule or a blister.

In a particular embodiment, the pharmaceutical composition is for use for treating hyperglycaemia and each unit dosage contains from 0.01 mg to 2 mg of a $K_{ATP}$ channel antagonist, preferably from 0.01 mg to 1 mg of glibenclamide.

In another particular embodiment, the pharmaceutical composition is for use for promoting growth and each unit dosage contains from 0.005 mg to 2 mg of a $K_{ATP}$ channel antagonist, preferably from 0.005 mg to 1 mg of glibenclamide.

The pharmaceutical composition may be in a liquid form and comprising from 0.1 mg/mL to 10 mg/mL a $K_{ATP}$ channel antagonist, preferably from 0.5 to 8 mg/mL of glibenclamide.

In another aspect, the present invention concerns the use of a $K_{ATP}$ channel antagonist for the preparation of a medicament suitable for enteral administration for treating hyperglycaemia and/or promoting growth in preterm and/or SGA infants. The present invention also concerns the use of a $K_{ATP}$ channel antagonist for the preparation of a medicament for treating hyperglycaemia and/or promoting growth in preterm and/or SGA infants by enteral route.

All embodiments disclosed above for the pharmaceutical composition are also encompassed in this aspect.

In a further aspect, the present invention concerns a method for treating hyperglycaemia and/or promoting growth in preterm and/or SGA infants, wherein the method comprises enterally administering a therapeutically effective amount of a $K_{ATP}$ channel antagonist to infants in need thereof.

All embodiments disclosed above for the pharmaceutical composition are also encompassed in this aspect.

In this aspect, by a "therapeutically effective amount" is intended an amount of $K_{ATP}$ channel antagonist administered to an infant that is sufficient to treat hyperglycaemia and/or promoting growth, preferably without inducing hypoglycaemia.

The amount of $K_{ATP}$ channel antagonist to be administered has to be determined by standard procedure well known by those of ordinary skill in the art, in particular by paediatrician. Physiological data of the infant (e.g. age, size, weight, gestational age at birth), the route of administration (by mouth or feeding tube), and the disease to be treated (hyperglycaemia and/or growth restraint) have to be taken into account to determine the appropriate dosage.

In an embodiment, the method of the invention comprises administering from 0.02 to 0.5 mg/kg of body weight/day of a $K_{ATP}$ channel antagonist to said infant. In a preferred embodiment, the method of the invention comprises administering 0.1 to 0.4 mg/kg of body weight/day of glibenclamide to said infant. Preferably, the $K_{ATP}$ channel antagonist is administered in two to four intakes per day.

In a particular embodiment, the preterm and/or SGA infant has hyperglycaemia and the method of the invention comprises administering 0.04 to 0.5 mg/kg of body weight/day of a $K_{ATP}$ channel antagonist to said infant. More particularly, the preterm and/or SGA infant has hyperglycaemia and the method of the invention comprises administering 0.04 to 0.4 mg/kg of body weight/day of glibenclamide to said infant, preferably 0.04 to 0.2 mg/kg of body weight/day.

In another particular embodiment, the growth of the preterm and/or SGA infant has to be promoted and the method of the invention comprises administering 0.02 to 0.25 mg/kg of body weight/day of a $K_{ATP}$ channel antagonist to said infant. More particularly, the growth of the preterm and/or SGA infant has to be promoted and the method of the invention comprises administering 0.02 to 0.2 mg/kg of body weight/day of glibenclamide to said infant, preferably 0.02 to 0.1 mg/kg of body weight/day.

In an embodiment, the method of the invention comprises administering from 0.02 to 0.5 mg/kg of body weight/day of a $K_{ATP}$ channel antagonist to said infant during at least seven days. In a particular embodiment, the infant is treated during at least two weeks, at least one month, at least two months or at least three months. Preferably, the infant is treated during less than one year, more preferably during less than six months.

Further aspects and advantages of the present invention will be described in the following examples, which should be regarded as illustrative and not limiting.

EXAMPLES

Use of a KATP Channel Antagonist for Treating Hyperglycaemia in a Premature Low Birth Weight Infant Continuous glucose infusion is always required in preterm infants to maintain glucose level. However, under such conditions neonatal hyperglycemia is commonly observed during the first week of life. There are also many conditions that are associated with neonatal hyperglycaemia such as stress or drug treatment by steroids or methylxanthines.

In preterm low birth weight infants, glucose infusion should be maintained at a rate of at least 4 to 7 mg/kg/min to match basal glucose requirement (Farrag et al., 2000).

Reducing glucose infusion to an extremely low rate to manage hyperglycemia significantly reduces caloric and protein intakes. Depriving these neonates of protein and carbohydrate substrates may have long-term effects on their growth and development.

The blood glucose concentration in preterm infants may be monitored by capillary blood determination in order to detect hypo- and hyperglycaemia. If possible, the technique of continuous glucose monitoring by inserting a sensor in the interstitial tissue is used.

When the blood glucose concentration exceeds 12 mmol/L (215 mg/dL), the preterm infants receive 0.1 mg/kg twice daily of glibenclamide to stimulate their endogenous insulin secretion. A liquid formulation of glibenclamide is administered directly into the stomach of the infant, preferably using minimal enteral feeding gastric tube.

The blood glucose concentration should be maintained within an acceptable range (i.e. 5.5 to 8.25 mmol/l). If hyperglycaemia is persisting or if no hypoglycaemia is detected, the dose of glibenclamide is increased (i.e. 0.2 mg/kg twice daily). On the contrary, if hypoglycaemia is detected, the dose of glibenclamide is reduced (i.e. 0.05 mg/kg twice daily). The dose of glibenclamide is thus adapted thanks to the continuous blood glucose monitoring.

Glibenclamide is administered during at least one week. The duration of the treatment depends on the prematurity and the weight of the infant. The treatment can be stopped as soon as hyperglycaemia is no longer detected.

Use of a $K_{ATP}$ Channel Antagonist for Promoting Growth of a Premature and/or Small-for-Gestational-Age Infant A large proportion of preterm infants show evidence of postnatal growth impairment irrespective of whether birth weight was appropriate or small for gestational age. The timing and magnitude of catch-up growth is very variable and long term studies suggest that final height may be significantly affected.

Glibenclamide can be administered to small for gestational age infants immediately after birth. For appropriate for gestational age infants, glibenclamide can be administered as soon as postnatal growth impairment is detected.

The infants receive 0.05 mg/kg twice daily of glibenclamide to promote their growth. Glibenclamide is administered in the form of a liquid formulation, preferably directly into the stomach of the infant, for example by using minimal enteral feeding gastric tube.

The efficiency of the treatment on the growth of infants is assessed by measuring the length, the head circumference and the weight of the baby every day, two days or every week.

Due to the insulin secretagogue activity of glibenclamide, the blood glucose concentration of treated infants is monitored, for example by capillary blood determination, in order to detect hypoglycaemia. If possible, the technique of continuous glucose monitoring by inserting a sensor in the interstitial tissue is used.

The blood glucose concentration should be maintained within an acceptable range (i.e. 5.5 to 8.25 mmol/l). If hypoglycaemia is detected, the dose of glibenclamide is reduced (i.e. 0.02 mg/kg twice daily). On the contrary, if no hypoglycaemia is detected, the dose of glibenclamide is increased (i.e. 0.1 mg/kg twice daily). The dose of glibenclamide is thus adapted thanks to the continuous blood glucose monitoring.

Glibenclamide is administered during at least one week, preferably one or two months. The duration of the treatment depends on the growth curve of the infant. The treatment can be stopped as soon as this growth curve corresponds to normal values.

REFERENCES

Albertsson-Wikland et al. Horm Res. 1998; 49 Suppl 2:7-13.
Beardsall et al., J. Pediatr 2007; 151: 611-7
Beardsall et al., N Engl J Med. 2008 Oct. 30: 359(18): 1873-84
Beardsall and Dunger. Early Hum Dev. 2008 December; 84(12):839-42
Farrag et al., Clin Perinatol 2000; 27:1-22.
Finken et al., Pediatrics 2006, 118:640-3
Leger et al., Pediatr Res. 1996 July; 40(1):101-7.
Mitanchez. Horm Res. 2007; 68(6):265-71
Mitanchez. Arch Pediatr. 2008 January; 15(1):64-74.
Weinhaus et al. J Clin Endocrinol Metab. 2003 June; 88(6):2753-9.
Woods et al. N Engl J Med. 1996 Oct. 31; 335(18):1363-7.

The invention claimed is:

1. A method for promoting growth in a preterm and/or small-for-gestational-age infant in need of growth promotion, comprising enterally administering a pharmaceutical composition comprising a therapeutically effective amount of a $K_{ATP}$ channel antagonist selected from the group consisting of glibenclamide, acetohexamide, carbutamide, glibornuride, chlorpropamide, tolbutamide, tolazamide, glipizide, gliclazide, gliquidone, glyclopyramide, glisoxepide, glimepiride, repaglinide, nateglinide, mitiglinide and combinations thereof to the preterm and/or small-for-gestational-age infant, wherein the pharmaceutical composition is administered to the infant for a period of seven days to six months and the growth of said preterm and/or small-for-gestational-age infant is promoted.

2. The method of claim 1, wherein the infant weighs less than 2,500 g at birth.

3. The method of claim 1, wherein the infant weighs less than 1,500 g at birth.

4. The method of claim 1, wherein the infant is born at less than 32 weeks gestation.

5. The method of claim 1, wherein the infant is born at less than 28 weeks gestation.

6. The method of claim 1, wherein the infant is a premature appropriate-for-gestational-age infant with preterm growth restraint.

7. The method of claim 1, wherein the $K_{ATP}$ channel antagonist is selected from the group consisting of glibenclamide, acetohexamide, carbutamide, glibornuride, chlorpropamide, tolbutamide, tolazamide, glipizide, gliclazide, gliquidone, glyclopyramide, glisoxepide, glimepiride, repaglinide, nateglinide and mitiglinide.

8. The method of claim 1, wherein the $K_{ATP}$ channel antagonist is glibenclamide.

9. The method of claim 1, wherein the pharmaceutical composition is in a liquid form.

10. The method of claim 1, wherein the pharmaceutical composition is a suspension of micronized particles of the $K_{ATP}$ channel antagonist.

11. The method of claim 1, wherein the preterm and/or small-for gestational-age infant is younger than 6 months.

12. The method of claim 1, wherein said pharmaceutical composition comprises a therapeutically effective amount of said $K_{ATP}$ channel antagonist and a surfactant.

13. The method of claim 12, wherein said surfactant is polysorbate 80 or ethoxylated castor oils.

14. The method of claim 1, wherein the pharmaceutical composition is administered to said infant for a period of two weeks to six months.

15. The method of claim 1, wherein the pharmaceutical composition is administered to said infant for a period of one to six months.

* * * * *